United States Patent
Grübl

(10) Patent No.: US 11,606,654 B2
(45) Date of Patent: Mar. 14, 2023

(54) DEVICE FOR TREATING A TINNITUS AFFLICTION

(71) Applicant: Klaus Grübl, Braunau am Inn (AT)

(72) Inventor: Klaus Grübl, Braunau am Inn (AT)

(*) Notice: Subject to any disclaimer, the term of this patent is extended or adjusted under 35 U.S.C. 154(b) by 0 days.

(21) Appl. No.: 16/970,626

(22) PCT Filed: Feb. 15, 2019

(86) PCT No.: PCT/EP2019/053766
§ 371 (c)(1),
(2) Date: Dec. 14, 2020

(87) PCT Pub. No.: WO2019/158674
PCT Pub. Date: Aug. 22, 2019

(65) Prior Publication Data
US 2021/0099817 A1 Apr. 1, 2021

(30) Foreign Application Priority Data
Feb. 15, 2018 (AT) .............. A 50144/2018

(51) Int. Cl.
| A61F 11/06 | (2006.01) |
| G02C 11/06 | (2006.01) |
| H04R 25/00 | (2006.01) |
| A61F 11/14 | (2006.01) |
| A61F 11/30 | (2022.01) |

(52) U.S. Cl.
CPC .............. *H04R 25/75* (2013.01); *A61F 11/14* (2013.01); *A61F 11/30* (2022.01)

(58) Field of Classification Search
CPC .. H04R 2460/13; H04R 25/75; A63B 2225/60

USPC .......................................... 381/312, 327, 72
See application file for complete search history.

(56) References Cited

U.S. PATENT DOCUMENTS

| 2005/0251226 | A1* | 11/2005 | D'Angelo | H04R 25/75 |
| | | | | 607/57 |
| 2012/0237075 | A1* | 9/2012 | East | H04R 17/00 |
| | | | | 381/381 |
| 2017/0303031 | A1 | 10/2017 | Barry | |
| 2018/0306659 | A1* | 10/2018 | Wade | G01L 9/0044 |
| 2019/0203549 | A1* | 7/2019 | Parthasarathy | E21B 21/08 |

FOREIGN PATENT DOCUMENTS

| AT | 8023 U1 | 12/2005 |
| CN | 205598091 | 9/2016 |
| CN | 206743497 | 12/2017 |
| DE | 2910315 | 9/1980 |

(Continued)

OTHER PUBLICATIONS

Office Action dated Nov. 18, 2022 in EP Patent Application No. 19708950.1, 13 pages.

*Primary Examiner* — George C Monikang
(74) *Attorney, Agent, or Firm* — Loza & Loza, LLP; Michael F. Fedrick

(57) ABSTRACT

The invention relates to a device for the treatment of a tinnitus condition, comprising a pressure point body which is dimensioned so that it can be secured to or in the vicinity of the auricle, characterized in that said pressure point body has a fastening element and a pressure element, whereby the position of the auricle is changed and/or the middle ear is deformed.

8 Claims, 8 Drawing Sheets

(56) References Cited

FOREIGN PATENT DOCUMENTS

| | | |
|---|---|---|
| GB | 2450931 | 1/2009 |
| JP | H03142414 | 6/1991 |
| JP | H0956774 | 3/1997 |
| JP | 3164048 U | 11/2010 |
| WO | 2015164889 | 10/2015 |

\* cited by examiner

Fig. 10

| ForgTin Online Study | Exit the survey and delete answers |

\* Please enter your e-mail address.

Your answer [                                    ]

\*

How loud do you perceive your tinnitus currently?

(from 0 = not at all to 10 = very loud)

\*

How burdensome do you perceive your tinnitus at the moment?

(from 0 = not at all to 10 = very burdensome)

\* At the moment, do you wear the ForgTin at your eyeglasses?

- ○ Yes, on the left
- ○ Yes, on the right
- ○ Yes, on both sides
- ○ No

DEVICE FOR TREATING A TINNITUS AFFLICTION

TECHNICAL FIELD

The invention relates to a device for the treatment of a tinnitus condition.

PRIOR ART

Tinnitus is an auditory perception that is perceived on one or both sides in addition to the sound acting on the ear. This perception is based on a hearing impairment. The nature of the apparent noises is very diverse: the auditory impressions are described as humming or whistling, hissing, rustling, crackling or knocking.

Tinnitus affects the quality of life. Previous treatment methods (including various forms of acoustic stimulation, behavioral therapy approaches, combined therapy approaches that include acoustic stimulation and behavioral therapy elements (e.g., tinnitus retraining therapy), drug therapy methods, physiotherapy, magnetic and electrical brain stimulation methods) do not always work, or do not work good enough. For most of the therapies offered, there is no evidence of efficacy demonstrated in sufficiently large placebo-controlled studies.

For example, an ear device is described in the prior art that is, designed to balance rapid changes in pressure brought about by rapid changes in altitude on airplanes in order to prevent earache. GB2450931, for example, describes earmuffs in which the pressure can be regulated by using an air pump.

In the case of hearing protectors that are worn as sound insulation, heat accumulation occurs after prolonged use, which can lead to excessive perspiration. In order to allow air to be exchanged, a ventilation opening is provided on the hearing protection capsule. The air exchange is made possible by changing the volume of the capsule interior (DE2910315).

CN205598091 (U) describes a device comprising a pair of glasses, a Bluetooth headset and headphones. Using said device, environmental sounds, notes or music, for example, may be played in by means of a software for treating tinnitus.

WO2015164889 describes a headphone that is, in use, locatable within or near an ear canal of a user, and an ear loop to secure the earphone to the ear of the user. The ear loop comprises an inflatable bladder to better secure, in use, the earphone to the ear of the user. US20170303031 describes headphones comprising an inflatable mounting system to better secure the housing of the headphone to the human ear. CN206743497 describes a headphone with an inflatable swelling body, which, however, is attached inside the inner ear.

Tinnitus can be curable after all. The chances of a cure are good, especially in acute tinnitus. However, there are no exact numbers on how many tinnitus sufferers are healed and in what way. Tinnitus patients can consider themselves healed when their ringing in the ears has disappeared. Therefore, there is still a need for a targeted, sustained and successful treatment of tinnitus. The object of the present invention is therefore to provide a device and its use which do not have the disadvantages and deficiencies of the prior art. In particular, it is an object of the present invention to provide a method for the treatment of a tinnitus condition.

BRIEF SUMMARY OF THE INVENTION

The object is achieved by the independent claims. The present invention thus comprises a new device for the treatment of tinnitus, said device changing the position of the auricle and thus changing the entry angle of sound. This change at the outer ear alleviates and/or completely cures the tinnitus condition.

In particular, the present invention relates to a device for the treatment of a tinnitus condition comprising a pressure point body, wherein the device is dimensioned so that it can be secured to the auricle (outer ear), characterized in that the pressure point body has at least one fastening element and one pressure element, whereby the position of the auricle (outer ear) is changed.

An embodiment comprises the device as described herein, wherein the body is a pair of glasses or a mounting by means of a temple, or the like.

An embodiment comprises the device as described herein, wherein the pressure point body has a fixed size or is variably fillable.

An embodiment comprises the device as described herein, wherein the pressure point body is a gel pad.

An embodiment comprises the device as described herein, wherein the variably filled pressure point body is an air cushion.

An embodiment comprises the device as described herein, wherein the air cushion is individually fillable.

An embodiment comprises the device as described herein, wherein the device further comprises a means for individually adapting the pressure point body.

An embodiment comprises the device as described herein, wherein said means is an air pump, a compressor or a syringe.

An embodiment comprises the device as described herein, wherein the device further comprises a controller with memory.

An embodiment comprises the device for the treatment of a tinnitus condition, consisting of a pair of glasses, wherein at least one pressure point body is attached to one or to both eyeglass temples.

An embodiment comprises the device for the treatment of a tinnitus condition, consisting of the device which is dimensioned so that it can be secured to the auricle, and having at least one pressure point body, and optionally a means for individually adapting the variable pressure point body to its wearer, as well as an electronic controller with memory.

Furthermore, the present invention comprises the use of the device according to the invention for the treatment of a tinnitus condition.

An embodiment comprises the use of the device according to the invention for the treatment of a tinnitus condition, wherein the position of the auricle (outer ear) is changed by the device, in particular by the pressure point body.

Another embodiment comprises the use of the device according to the invention for the treatment of a tinnitus condition, wherein the entry angle of the sound at the outer ear is changed by the device, in particular by the pressure element.

Another embodiment comprises the use of the device according to the invention for the treatment of a tinnitus condition, wherein pressure is exerted on the auricle (outer ear) by the device, in particular by the pressure point body. By this pressure the middle ear can be deformed and the sound can be refracted differently.

Furthermore, the present invention comprises a method for the treatment of a tinnitus condition, comprising a device that is placed behind the auricle, said device being configured such that the position of the auricle of the outer ear is changed.

Another embodiment comprises a method for the treatment of a tinnitus condition as described herein, wherein pressure is exerted on the auricle and/or on the middle ear by said device, in particular by the pressure point body.

Another embodiment comprises a method for the treatment of a tinnitus condition as described herein, wherein in each case a device, in particular a pressure point body, is placed behind both auricles, wherein pressure is exerted on the auricles, in particular by the pressure point body.

Another embodiment comprises a method for the treatment of a tinnitus condition as described herein, wherein at least one device as described herein is placed behind one or both auricles.

BRIEF DESCRIPTION OF THE DRAWINGS

FIG. 10 is an illustration of a questionnaire.

DETAILED DESCRIPTION OF THE INVENTION

Figure 1:
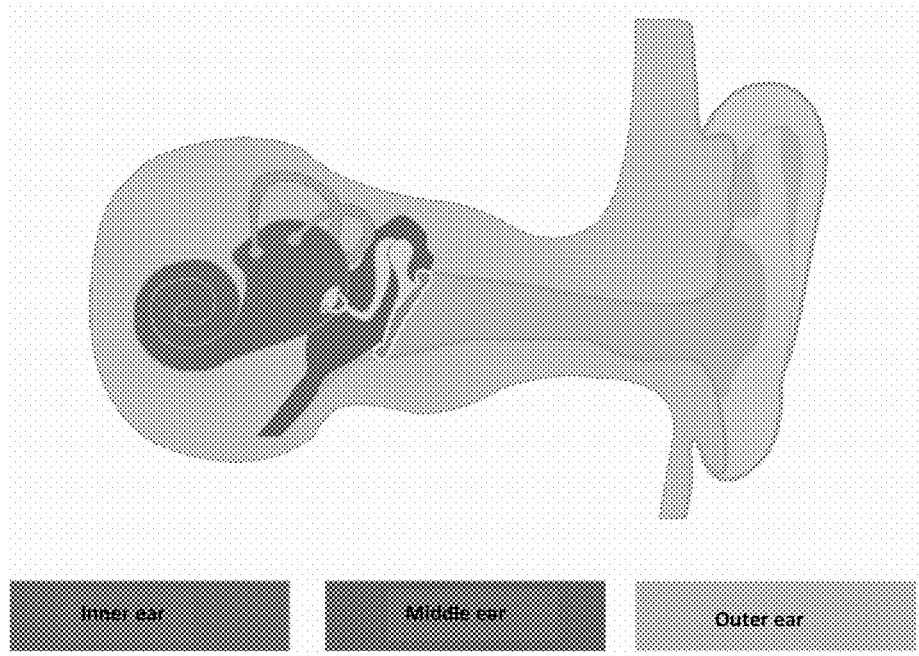
FIG. 1 shows a schematic representation of the ear.
Figure 2:
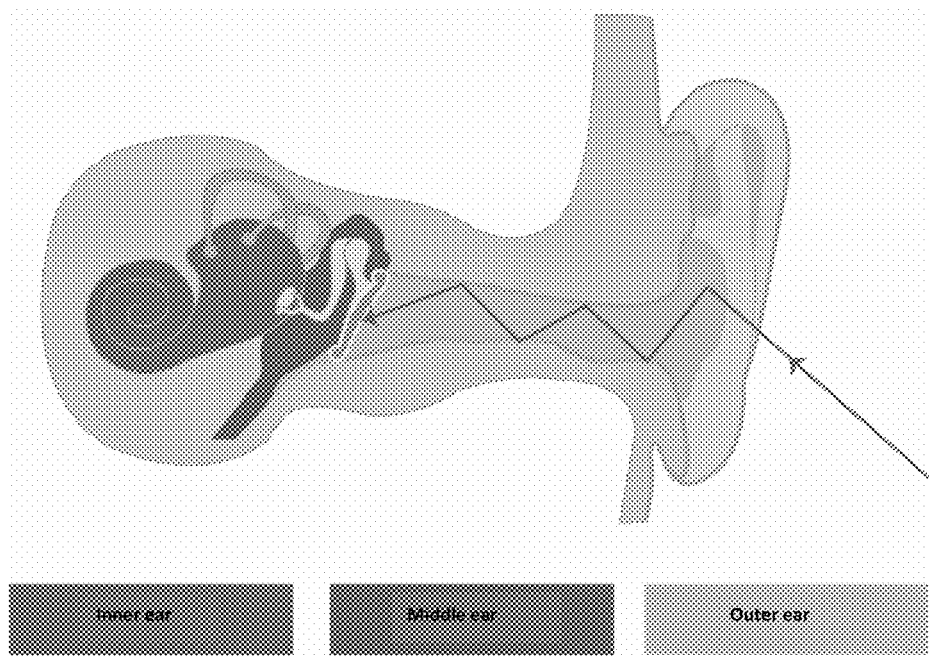
FIG. 2 shows a schematic representation of the ear with sound entry.
Figure 3:
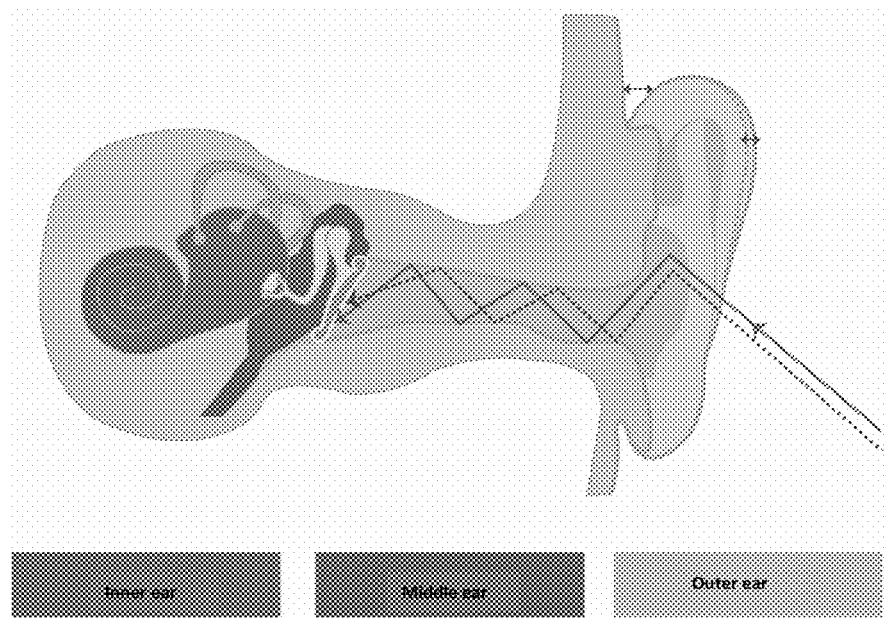
FIG. 3 shows a schematic representation of the ear with a changed sound entry.
Figure 4:
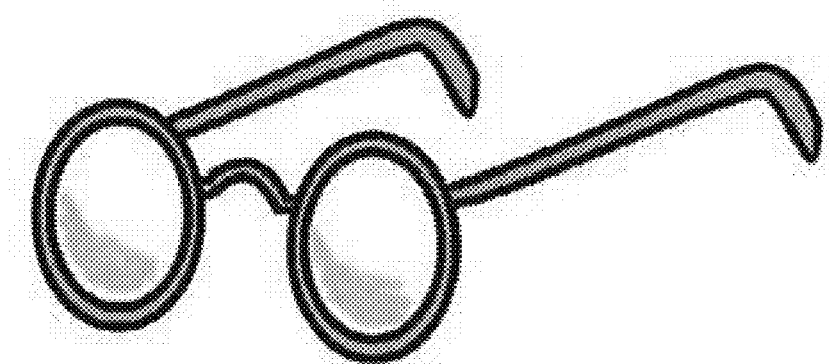
FIG. 4 shows a schematic diagram of a pair of glasses.

The ear consists of the outer, middle, and inner ear (see FIG. 1).

The outer ear comprises the ear cartilage, the auricle, the ear lobe and the external auditory canal or the ear canal and the eardrum outer layer. It not only serves to capture the sound, but also to encode a certain direction of incidence of the sound by spectral minima and maxima (see localization). The numerous elevations and depressions of the auricle form acoustic resonators, which are excited each time sound hits from a certain direction. This creates direction-dependent minima and maxima in the frequency spectrum of the ear signal, which are used by the ear to determine the directions of incidence such as top, bottom, front or rear (directional bands).

The middle ear includes the eardrum and the ossicles hammer, anvil and stirrup. The round window connects the scala tympani of the inner ear with the middle ear. The Eustachian tube, also called the ear trumpet, connects the middle ear and nasopharynx. A mechanical impedance conversion takes place in the middle ear, which enables an optimal transmission of the signal from the outer ear to the inner ear. Since the acoustic impedance of water is approximately 3000 times that of air, without the lever system formed by the ossicles, only a small part of the sound energy that reaches the eardrum would be passed on to the inner ear.

The inner ear is located in a small cavity system (bony labyrinth) within the petrous bone, a portion of the temporal bone. In said bony labyrinth the membranous labyrinth is located, consisting of the cochlea, in which sound is converted into nerve impulses, and the organ of equilibrium. The organ of equilibrium consists of the semicircular ducts and two vesicular portions, the utriculus and the sacculus. The organ of equilibrium is used to detect changes in movement and the direction of gravity. The cochlea and the organ of equilibrium are of similar construction: both are filled with two common parallel fluid systems (perilymph and endolymph) and have hair cells. The hair cells are cylindrical and are named after the approximately 30 to 150 hair-like extensions at the upper end of the cell (stereocilia). The hairs are bent by movements of the fluid and thereby trigger nerve impulses. At the lower end there is a synapse with a sensory neuron. Said synapse releases neurotransmitters even in the resting state. If the hair extensions are deflected by sound vibrations or changes in the movement of the head, the amount of neurotransmitters changes. In the organ of equilibrium, the hair extensions are covered with a kind of gelatinous layer, on which small crystals of calcium carbonate are deposited, which intensify the effect of movements. From the cochlea, the auditory nerve together with the nerve bundles of the organ of equilibrium extend towards the brain as the vestibulocochlear nerve.

The effects of tinnitus strongly depend on the subjective perception and assessment of the ringing in the ears. Ringing in the ears can occur on one or both sides.

Tinnitus aurium means "ringing in the ears". Medically, tinnitus is defined as an acoustic perception that arises from outside the body without a corresponding acoustic stimulus and has no information content.

A distinction is made in principle between two forms. In the case of objective tinnitus, there is a body's own sound source in the ear or near the ear, whose sound emissions are perceived. This means that the sounds that often emanate from the blood vessels or the muscles actually exist and can therefore also be heard by others, even if mostly only with a stethoscope or other medical devices.

Much more common, however, is subjective tinnitus. Here, those affected perceive sounds and noises that cannot be attributed to a physical sound source and therefore cannot be heard by other people. But this does not mean that the patients only imagine the humming, buzzing, whistling, ringing, rustling or knocking. Rather, subjective tinnitus is due to incorrect information formation or processing in the auditory system, which extends from the ear via the auditory nerve to the hearing centers in the brain.

For many of those affected, however, it is not possible to determine definitely the cause of the ringing in the ears. This is called idiopathic tinnitus.

Surprisingly, it has now been found that by changing the position of the outer ear relative to the rest of the ear, the sound is changed, that is to say, the sound is refracted compared to the "normal entry". This leads to a different point of impact on the eardrum. As a result, the hammer (handle) of the first auditory bone is moved differently and sends changed pressure signals to the next auditory bones or then on to the cochlea. In the cochlea, the sensory hairs stored in a fluid are set in motion differently. This leads to a changed conversion of the electrical signals into the brain and to a change in the learning technology of the synapses—the previous sounds are no longer heard and thus "forgotten" in the long term.

Due to changes in the entry angle of sound, the ear noises (tinnitus) perceived as "bothering" are no longer perceived, since the sound impinges on the eardrum at other points of impact.

Sound changes frequency due to a different refraction (change in path length). Frequency change due to change in distance between observer (eardrum) and sound source (Doppler effect). The sound path in the ear between the outer ear and the eardrum changes. For that reason, the previous "old" frequencies, which were perceived as bothering, are no longer perceived, since they changed in terms of "frequency" and are no longer perceived in the brain. This will mainly occur at high frequencies.

Using the device according to the invention, the entry angle of sound is changed so that those affected no longer hear the previously learned bothering sounds. The device according to the invention therefore comprises a pressure point body which is dimensioned so that it can be secured to the auricle, and has at least one pressure element, wherein the position of the auricle is changed by the pressure body point. By changing the position of the outer ear by this pressure point body, the entry angle of the sound into the ear is therefore changed.

In particular, it is advantageous to apply pressure to the outer ear by the pressure point body. This pressure can result in that the position of the outer ear is changed so that the entry angle of the sound is also changed and thus bothering tinnitus sounds are no longer heard. The perception of noises that are not caused by acoustic signals from the environment is reduced or eliminated altogether with the device according to the invention.

The punctiform pressure point body can be attached to any conventional device which can be secured to the auricle. Depending on the configuration of the device, one or more punctiform pressure point bodies can be attached.

Conventional devices are, for example, eyeglass frames or simple ear hooks, as are used, for example, in headphones or hearing aids. An embodiment of the invention is, for example, a simple earpiece or an earpiece-like bracket that can be secured to the outer ear. Eyeglass frames are particularly suitable where, for example, the pressure point body or bodies can be attached to one or both eyeglass temples.

The term "punctiform" as used herein refers to a single location of the device, to which a pressure point body is attached. In particular, earphones can already have a swelling body which is, for example, of a ring-shaped form and thus covers the entire ear. One or more pressure point bodies may be attached in a punctiform manner so that the position of the auricle can be changed individually.

The pressure point body can be produced from different materials. In principle, any material can be used which is suitable for changing the usual position of the auricle. For example, the pressure point body can be made of plastic, fabric, felt, foam, gel, rubber, elastic tape or like materials. The pressure point body can be produced from a foamed material; from an elastic, deformable material, or from a plastic material, for example from polypropylene.

The pressure point body can have a fixed or a variable shape. In an embodiment, the pressure point body consists of a fastening element and a pressure element. In particular, the pressure point body can also consist of a pressure element, the fastening element being designed as an adhesive side of the pressure element. In this embodiment, the pressure point body is attached directly behind the auricle by means of the adhesive side. For this purpose, the adhesive side can have a surface coating, such as for example a rubber coating or an adhesive or glue coating.

Preferably, the fastening element has a cylindrical shape with a circular cross-sectional geometry. In cross section, however, the fastening element can also be oval, triangular, rectangular, square, polygonal, L-shaped or the like. This means that the fastening element can have any geometry in cross section. As a result, the fastening element can be attached to any locations on the device and thus adapted to the individual needs of the wearer. In another embodiment, the fastening element can be fixed to the device by means of a clip mechanism.

Another embodiment of the pressure point body comprises also a pressure element, which may have a fixed or a variable volume. For pressure elements with a variable volume, for example, pads that are filled with air, water, and/or generally with liquids as required, and can thus be optimally adapted to the needs of the wearer, are particularly suitable.

Pressure elements with a fixed volume and a fixed shape are preferably made of plastic.

Another embodiment, therefore, comprises the device according to the invention, which in addition to the pressure point body and the pressure element to be adapted variably, contains a miniature air pump, a (miniature) syringe or a miniature compressor for individually filling the pressure element. The miniature compressor can function by reciprocating, by rotating screws, by helical motion, by centrifugation or other methods. An embodiment also comprises a thermal change of the pressure element, for example by rubbing, kneading, pressing (i.e., mechanical effects), by increasing or lowering the temperature or the use of micropumps with a piezo membrane.

To adapt the setting of the variable pressure element optimally, it can be advantageous when the device has a controller with which the swelling body can be individually adapted to the needs of the wearer.

The controller may further have a memory, in which the status information of the swelling body is stored.

Exemplary Embodiments

The following exemplary embodiments illustrate the present invention without, however, limiting its scope.

Figure 5:
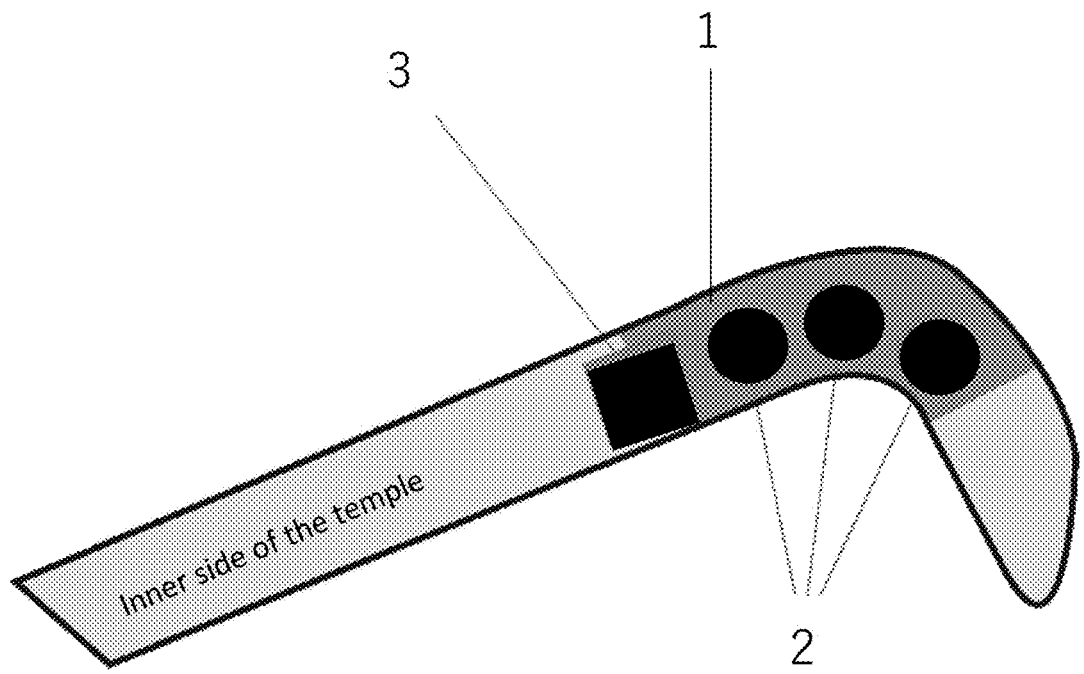
FIG. 5 shows a schematic diagram of an eyeglass temple with air chambers and control hardware.

An embodiment is shown in FIG. 5. It consists of an eyeglass temple (1) having three variable pressure point bodies (2) on the inner side of the temple. These variable pressure point bodies can be filled individually by the compressor (3).

Figure 6:
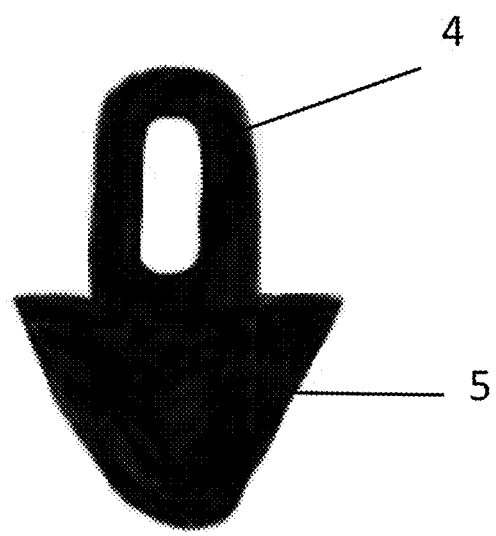
FIG. 6 shows a schematic pressure point body.

A pressure-point body (2) is schematically illustrated in FIG. 6. FIG. 6 shows a pressure point body (2) consisting of a fastening element (4) and a pressure element (5).

Figure 7:
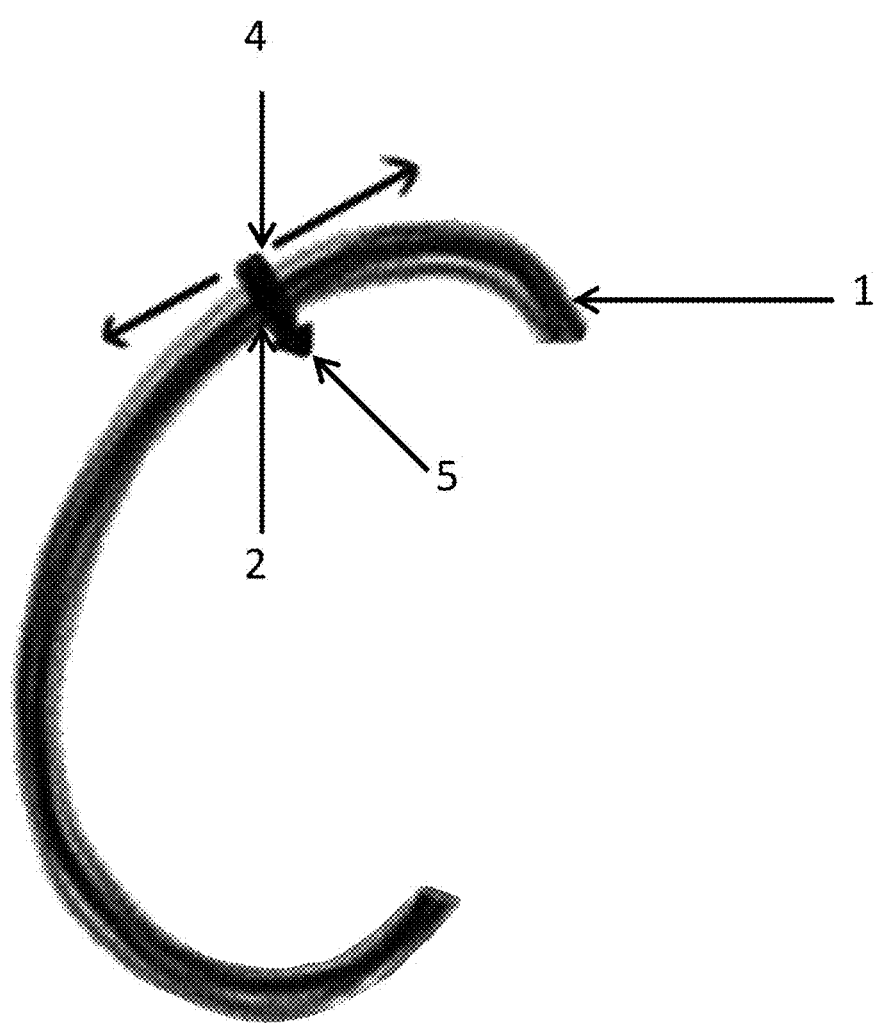
FIG. 7 shows a schematic representation of an earpiece with a pressure point body that can be fixed individually on the earpiece.
Figure 8:
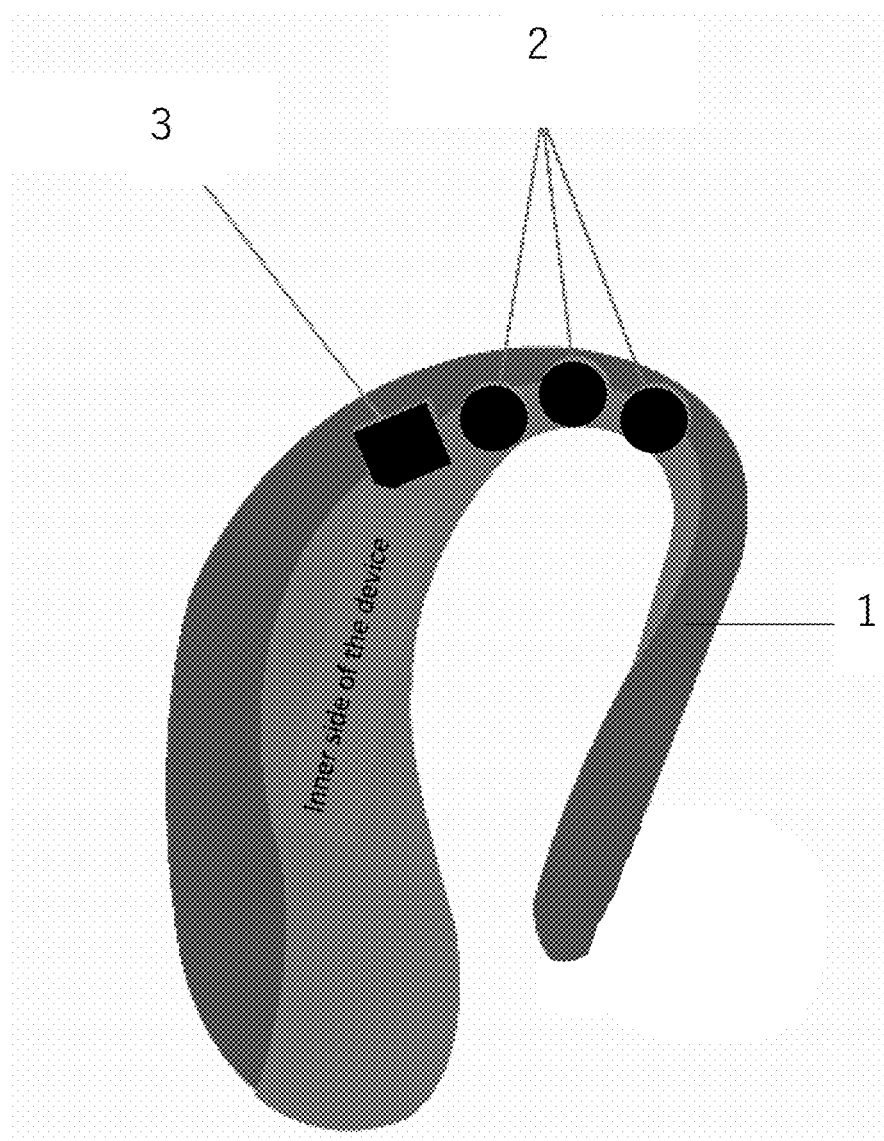
FIG. 8 shows a schematic representation of an earpiece with air chambers and control hardware.

FIG. 7 shows another embodiment consisting of an earpiece with a pressure point body. This pressure point body (2) consisting of a fastening element (4) and a pressure element (5) can be adapted individually according to the needs of the wearer, the pressure point body (2) being appropriately fixed to the earpiece to ensure an optimal and individual pressure application.

Case Studies

A first case study has already been carried out under the control of the inventor and applicant. The participants had to meet the following requirements to participate in the study:
  people whose tinnitus condition is considered to be medically incurable. That is to say, people who no longer respond to possible therapy;

eye glass wearers; and people agreeing to participate in an online survey twice a day.

In total, 7 participants who were selected in a doctors office by a general practitioner, participated in this first case study. A pressure point body was attached to the eyeglass temple of these study participants. This device according to the invention with the pressure point bodies was worn by the study participants for the most part throughout the entire day.

Figure 9A:
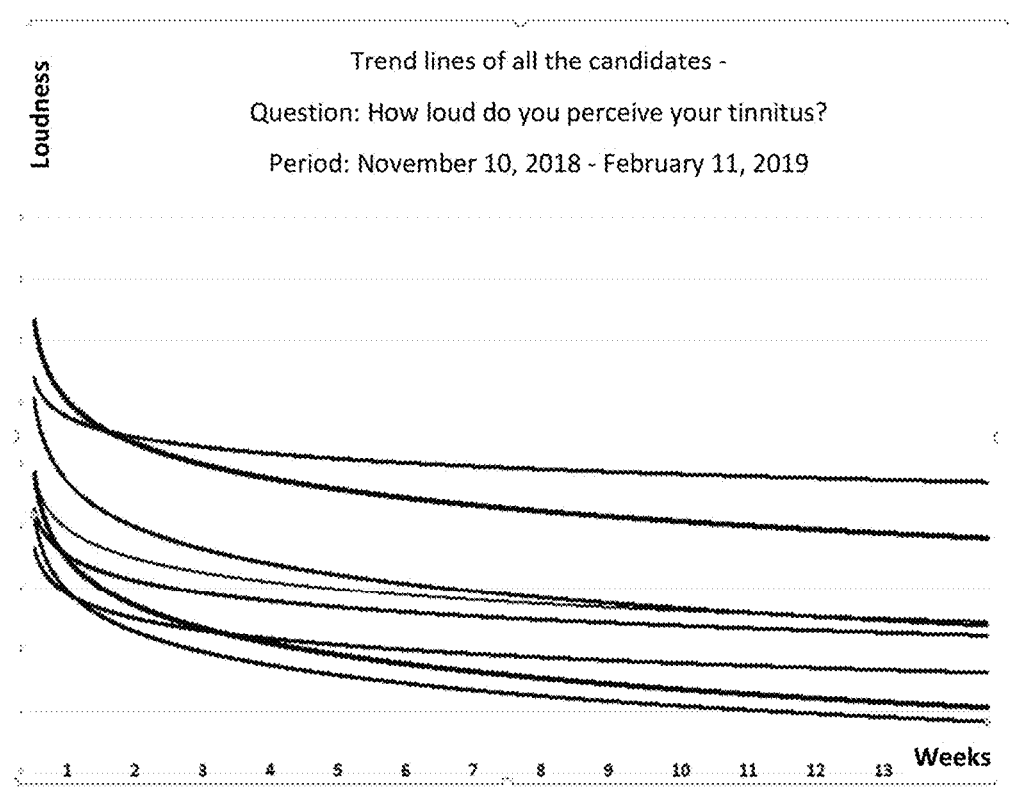
FIGS. 9A and 9B show the trend of the subjective perception of the study participants during the study period. The study participants had to rate their individual assessment of their tinnitus condition over the study period, with their subjective perception being entered according to a scale of values from 0=not burdensome/inaudible to 10=very burdensome/very loud. The trend lines were calculated logarithmically in Excel using the individual data per participant.
Figure 9B:
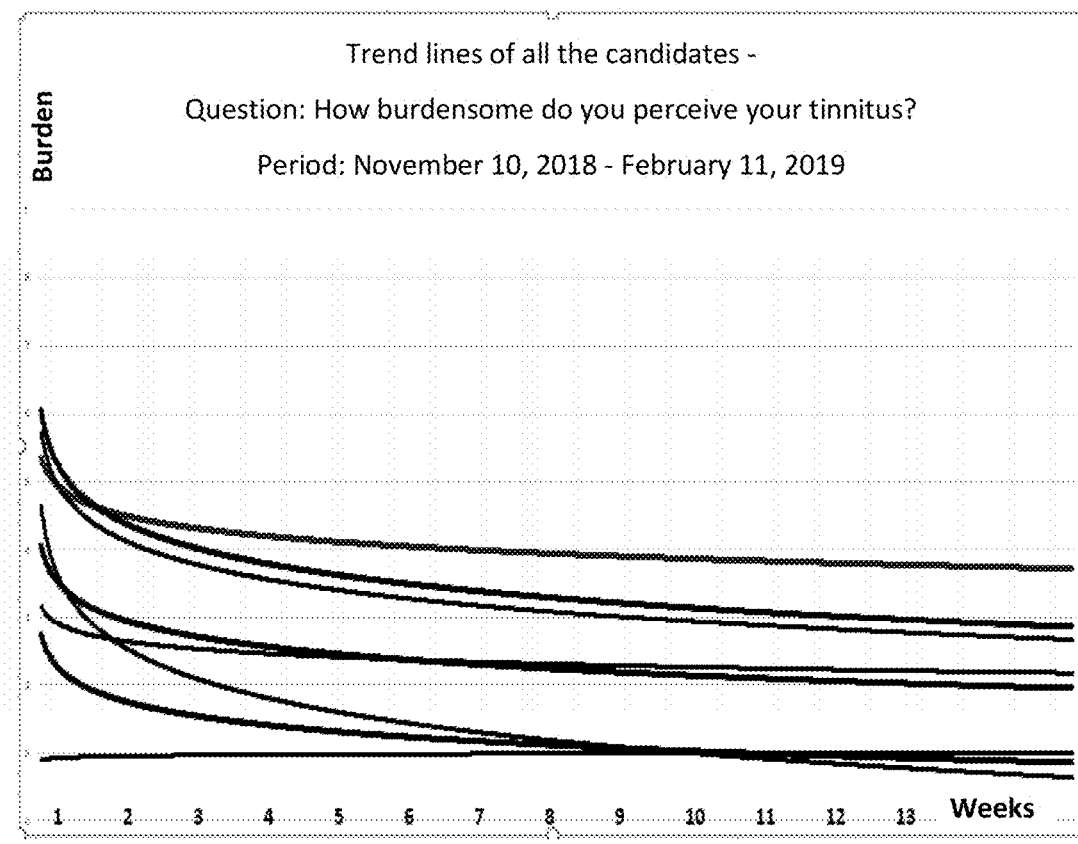

Within the study period of about 8 weeks, 70% of the patients experienced a significant improvement in the subjectively perceived tinnitus condition (see FIG. 9). For this purpose, the online survey of the study participants was evaluated over this period of time. The study participants were asked about their personal perception of the loudness of the tinnitus. For this purpose, they were asked to classify their personal assessment on a scale of values from 0=not heard at all to 10=very loud. Likewise, they were asked to classify the personal burden of their tinnitus in this scale of values from 0=not at all to 10=very burdensome.

The participants answered the questionnaire shown in FIG. 10 online, wherein ForgTin refers to the pressure point body.

The invention claimed is:

1. A method for the treatment of a tinnitus condition, comprising the step of placing a device behind an auricle of an ear of a subject, wherein pressure is exerted on the auricle by a pressure point body of the device, the pressure point body comprising a ring-shaped fastening element and a pressure element projecting from the fastening element, wherein the fastening element is secured to an earpiece, wherein the auricle of the subject is changed in position when the subject wears the earpiece, thereby changing the entry angle of sound into the ear and alleviating the tinnitus condition.

2. The method for the treatment of a tinnitus condition according to claim 1, wherein the middle ear is deformed by the pressure point body.

3. The method for the treatment of a tinnitus condition according to claim 1, wherein the device is placed behind both auricles of the subject.

4. The method for the treatment of a tinnitus condition according to claim 1, wherein the pressure element is a variably fillable body.

5. The method for the treatment of a tinnitus condition according to claim 4, wherein the variably fillable body is filled with air, gel or a liquid.

6. The method for the treatment of a tinnitus condition according to claim 1, wherein the pressure element is a gel pad or an air cushion.

7. The method for the treatment of a tinnitus condition according to claim 1, wherein the fastening element is a circular mounting element.

8. The method for the treatment of a tinnitus condition according to claim 1, wherein the pressure point body can be displaced variably on an inner side of the earpiece.

* * * * *